United States Patent [19]

Heinze

[11] Patent Number: 5,622,429
[45] Date of Patent: Apr. 22, 1997

[54] MEDICAL APPARATUS FOR TRANSFERRING DATA BETWEEN A DATA MONITORING UNIT AND A REMOTE DATA ANALYSIS UNIT VIA A CONTACTLESS MEMORY CARD

[75] Inventor: Werner Heinze, Finning, Germany

[73] Assignee: Jostra Medizintechnik GmbH & Co. KG., Hirrlingen, Germany

[21] Appl. No.: 184,971

[22] Filed: Jan. 21, 1994

[30] Foreign Application Priority Data

Jan. 21, 1993 [DE] Germany .......................... 43 01 524.7

[51] Int. Cl.⁶ ................................................ G06F 15/00
[52] U.S. Cl. ...................................... 395/200.08; 128/710
[58] Field of Search ........................ 364/413.01–413.12; 128/710–715; 395/200.08–200.09, 833, 893, 894, 442, 800

[56] References Cited

U.S. PATENT DOCUMENTS

| | | | |
|---|---|---|---|
| 4,245,331 | 1/1981 | Hamano et al. ........................ | 395/442 |
| 4,258,430 | 3/1981 | Tyburski ................................. | 395/180 |
| 4,361,877 | 11/1982 | Dyer et al. ........................ | 364/464.04 |
| 4,642,769 | 2/1987 | Petrofsky ................................. | 364/415 |
| 4,686,999 | 8/1987 | Snyder et al. ........................... | 128/716 |
| 4,754,401 | 6/1988 | Kaczynski et al. ................. | 364/413.03 |
| 4,895,161 | 1/1990 | Cudahy et al. ........................... | 128/710 |
| 5,086,778 | 2/1992 | Mueller et al. ........................... | 128/696 |
| 5,291,399 | 3/1994 | Chaco ................................. | 364/413.02 |
| 5,295,485 | 3/1994 | Shinomura et al. ............... | 128/660.07 |
| 5,421,343 | 6/1995 | Feng ........................................ | 128/710 |

FOREIGN PATENT DOCUMENTS

| | | |
|---|---|---|
| 0467693 | 1/1992 | European Pat. Off. . |
| 2660089 | 9/1991 | France . |
| 3833617 | 4/1989 | Germany . |

OTHER PUBLICATIONS

Annual Int. Conference of the IEEE Engineering in Medicine and Biology Society, vol. 12, No. 3, 1990, pp. 1262–1263.

*Primary Examiner*—Lance L. Barry
*Attorney, Agent, or Firm*—Michael J. Striker

[57] ABSTRACT

The medical apparatus for an operating room, especially a heart-lung machine, includes an electrically-powered device for producing data and performing operation steps and a data monitoring and analysis device which is divided into a data monitoring unit and a data analysis unit which is separate from the data monitoring unit and can be located outside the operating room in which the electrically-powered device and monitoring unit are located. The data monitoring unit (14) includes a portable and removable memory card (20). Both the data monitoring unit (14) and the data analysis unit (15) have a receiving slot device in which the memory card can be inserted and held so that data can be transferred between the units (14) and (15) by carrying the memory card from one unit to the other. Thus the data analysis unit (15) can be used with many different types of electrically-powered devices used in the operating room and can be easily located outside of the operating room. Also additional space is freed in the operating room by the arrangement according to the invention.

7 Claims, 2 Drawing Sheets

MEDICAL APPARATUS FOR TRANSFERRING DATA BETWEEN A DATA MONITORING UNIT AND A REMOTE DATA ANALYSIS UNIT VIA A CONTACTLESS MEMORY CARD

BACKGROUND OF THE INVENTION

The present invention relates to a medical apparatus and, more particularly, a unit for an operating room, especially a heart-lung machine.

A medical apparatus or unit for an operating room, particularly a heart-lung machine, is known including an electrically-powered device for generating data and/or controlling and/or performing operation steps and a data monitoring and analysis means connected with it. The data monitoring and analysis means is provided with at least one microprocessor having at least one keyboard input device, at least one display device and an electronic data storage means.

Medical devices or operating room units of this type, which are used for difficult procedures and have a complicated structure, are provided with data analysis means, which, among other things, record measured data and later review it as well as follow the course of the procedure. Currently this data analysis means is provided with a PC (Personal Computer), together with the electrically-powered device for controlling and performing the operating steps, e.g. in a heart-lung machine, in the operating room, and is connected by a bunch of electrical conductors with the remaining electronic control devices and units. This is in many cases disadvantageous. The personal computer must be modified electrically according to the most rigorous safety requirements of the operating room and it must have a special protective housing. It increased spatial requirements and requires structural features for making the numerous electrical connections of the connecting cables so that they do not hinder the medical team performing the procedure in the operating room.

SUMMARY OF THE INVENTION

It is an object of the present invention to provide a medical apparatus or an operating room unit of the above-described type, especially a heart-lung machine, which has a compact spatial structure without obstructing freely-lying connecting conductors or cables in the operating room.

This object and others which will be made more apparent hereinafter is attained in a medical apparatus or an operating room unit, including an electrically-powered device for generating data and/or controlling and/or performing operating steps and data monitoring and analysis means connected with it. The data monitoring and analysis means is provided with at least one microprocessor having at least one keyboard input device, at least one display device and an electronic storage means.

According to the invention the data monitoring and analysis means consists of a data monitoring unit and a data analysis unit separate from the data monitoring unit so that the data analysis unit can be put in a different room than the operating room in which the data monitoring unit and electrically-powered device work. The data analysis unit is provided with a microprocessor and the data monitoring unit has at least one portable and removable memory card for transfer of data between the data monitoring unit and the data analysis unit.

The medical apparatus according to the invention has a more compact and space-saving structure than that of the prior art, because bulky connecting cables which hinder the operating team in the operating room are replaced by the portable memory card. Furthermore a more logical and flexible working procedure can be developed using the apparatus according to the invention. The data analysis unit can be located in a dry area outside of the operating room so that special protective features can be abandoned and normal commercially obtainable computer equipment can be used for the data analysis unit. One data analysis unit is sufficient for a number of different electrically powdered devices used for different medical procedures, which generate data that is easily transported and fed to the data analysis unit by the portable memory card in a reliable manner. Also the replacement of medical apparatus during an operating procedures is easier and a rapid transfer of data via the portable memory card to the new replacing device in the operating room allows the procedure to continue in a rapid and reliable manner. The preparation of the electrically-powered device performing needed steps in the operating room does not need to occur in the operating room itself in the apparatus according to the invention, but instead the memory card can be provided with the required patient data outside of the operating room and then this card is input into the electrically-powered device in the operating room.

The data analysis unit can also advantageously be provided by a comparatively simple personal computer with a receiving slot device for the memory card. The data monitoring unit can also have a display screen for data generated by the electrically-powered device performing operating steps and/or collecting data or for fixed data, e.g. patient data, stored on the memory card. Thus a reliable control is provided to make certain that the correct memory card is used for the medical procedure in progress in the operating room, because the operating room team can continuously observe the important data on the display screen. Advantageously also the data monitoring unit separate from the data analysis unit can have a key input device for manual operation or control of the display screen and/or the electrically powdered device for collecting data and/or controlling operating steps, to which individual memory locations on the memory card are allocated. Thus the data monitoring unit allows an additional and documented change and adjusting of predetermined values or the following of operation steps. The memory card has advantageously special memory locations for predetermined fixed data and memory locations for perfusion data generated by the electrically-powered device, so that the data on the memory card can be influenced by and depends on a clock circuit means.

BRIEF DESCRIPTION OF THE DRAWING

In the following detailed description one embodiment example of the medical apparatus according to the invention, namely a heart-lung machine, is illustrated in detail, with the aid of the accompanying drawing in which.

DESCRIPTION OF THE PREFERRED EMBODIMENT

Figure 1:
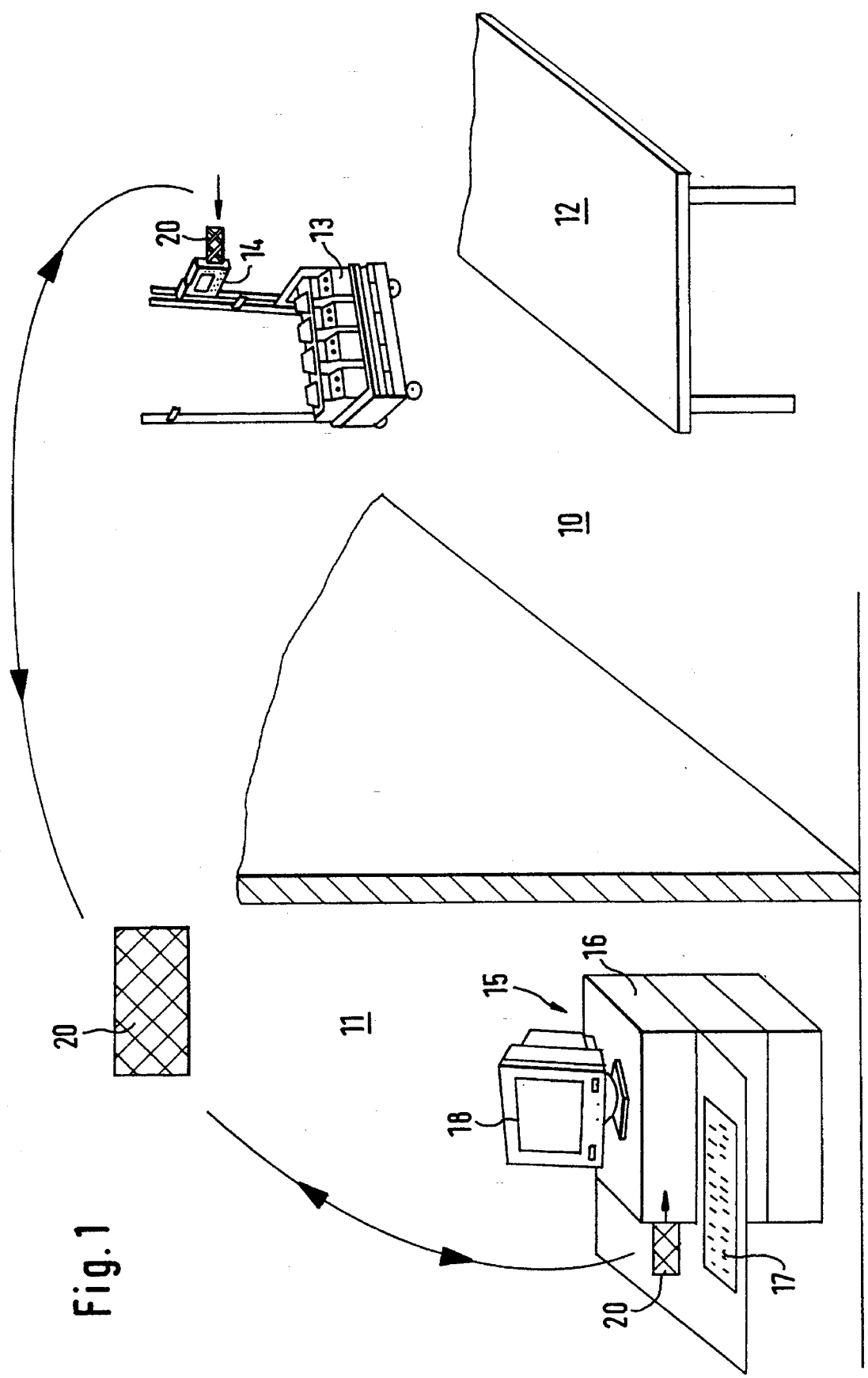
FIG. 1 is a schematic perspective view of an electrically separate arrangement of means for electronic data monitoring and data analysis in the heart-lung machine according to the invention.

FIG. 1 shows an operating room 10 and another adjacent room 11 of a clinic. An electrically-powered device (13) for performing and controlling operation steps and producing data of the heart-lung machine and an operating table 12 are in the operating room 10. The electronic data monitoring and data analysis means of the heart-lung machine is divided into two electrically separate units, namely a data monitoring unit 14 located in the operating room 10 and a data analysis unit 15 located in the other adjacent room 11 of the clinic. The data analysis unit 15 comprises a commercial personal computer 16 with a keyboard input device 17 and a display device 18. The coupling means between both units 14 and 15 is a portable and removable data memory in the form of at least one memory card 20 without external contacts. During operation of the electrically-powered device 13 in the operating room 10, this memory card 20 is located in the data monitoring unit 14. The memory card 20 is inserted in the data analysis unit 15 in the other adjacent room 11 for the data analysis and also for loading of fixed data regarding the patients and the medical apparatus units or devices.

Figure 2:
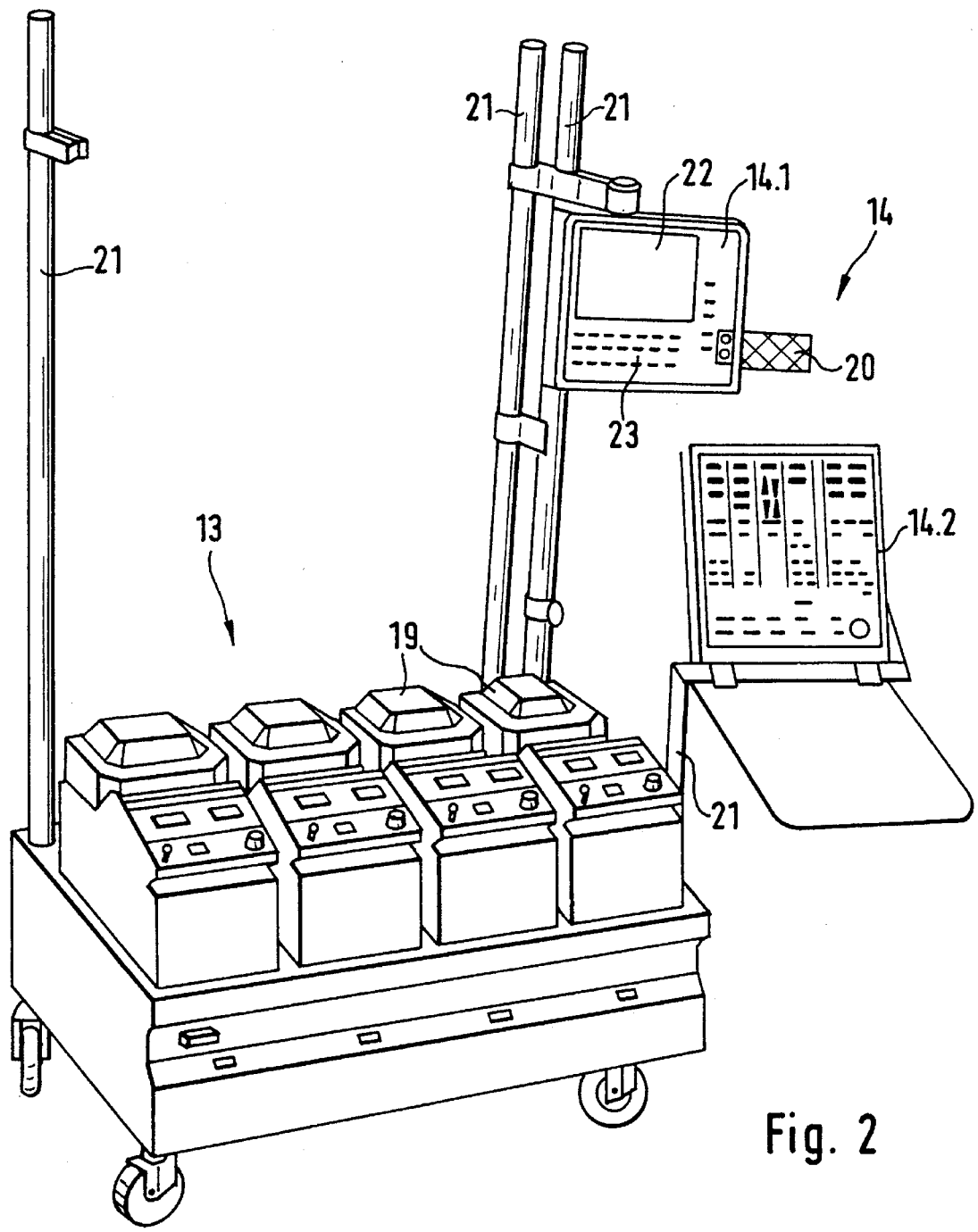
FIG. 2 is a perspective view of an electrically-powered device for controlling and performing operation steps and generating data of the heart-lung machine according to the invention which remains in the operating room during a surgical procedure performed with the heart-lung machine.

FIG. 2 shows the electrically-powered device 13 with the electronic data monitoring unit 14 in greater detail. The electrically-powered device of the heart-lung machine 13 is equipped with four pumps 19. The electrical control cables between these pumps 19 and the other apparatus components of the heart-lung machine in the electronic data monitoring unit 14 are guided to the exterior electrically shielded by the supporting mast 21 of the movable heart-lung machine. The electronic data monitoring unit 14 comprises the devices 14.1 and 14.2, in the embodiment example shown in the drawing. The device 14.1 is a flat display device comprising the display screen 22, a key input means 23 and a receiving slot device for the memory card 20. The key input means 23 includes a so-called action key, by which special data occurring during the course of an operation or found in the internal memory or found on the memory card 20 are retrieved for representation on the display screen 22 or for changing the data. The memory card 20 itself is divided into different memory blocks of memory locations, which either store perfusion data generated during the operation or fixed data input already prior to the operation, or are associated with the action key. The device 14.2 of the electronic data monitoring and data storage unit 14 has predominantly operator keys and indicator devices for individual apparatus components. A clock circuit means of the electronic apparatus can be accommodated either in the device 14.1 or 14.2 and can be used to change or modify the contents of the memory locations on the memory card 20.

All four pumps 19 of the heart-lung machine shown in the drawing, as also other unillustrated electrically operating or monitored apparatus components, are arranged so that they are exchangeable or replaceable by plug coupling devices to avoid the freely lying connecting cables, of which one coupling device part is arranged directly on the apparatus component and another coupling device part is on the part that holds the apparatus component or the supporting housing of the heart-lung machine.

While the invention has been illustrated and described as embodied in a medical apparatus for an operating room, particularly a heart-lung machine, it is not intended to be limited to the details shown above, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

I claim:

1. A medical apparatus for an operating room, said medical apparatus comprising electrically-powered means (13) for generating data regarding operation steps in the operating room and for at least one of controlling and performing said operation steps in the operating room, data monitoring means (14) for monitoring and collecting said data generated by said electrically-powered means (13), said data monitoring means (14) being located in the operating room during the performing of the operation steps; data analysis means (15) for analyzing said data collected and monitored by said data monitoring means (14), said data analysis means (15) being separate from said data monitoring means (14) and located in another room different from said operating room, wherein said data analysis means (15) includes at least one microprocessor with data storage means, at least one display device and at least one keyboard input device; and means for transferring data between said data monitoring means (14) and said data analysis means (15), said means for transferring data solely consisting of at least one portable and removable memory card (20) so that connecting cables for said data transfer electrically connecting the data analysis means (15) with the data monitoring means (14) are eliminated;

wherein said data monitoring means includes means for releasible electrical connection of said at least one portable and removable memory card (20) with said data monitoring means (14) to receive said data from said data monitoring means (14) and said data analysis means (15) includes means for releasible electrical connection of said at least one portable and removable memory card (20) with said data analysis means (15) to transfer said data to said data analysis means;

wherein said at least one portable and removable memory card (20) has no external electrical contacts so that transfer of said data between said data monitoring means (14) and said data analysis means (15) is contactless and said data analysis means (15) comprises a personal computer (16) with a receiving slot device in which said at least one portable and removable memory card (20) is insertable after removal from said data monitoring means (15).

2. The medical apparatus as defined in claim 1, wherein said data monitoring means (14) includes a display screen (22) for display of fixed data stored in said at least one portable and removable memory card (20) and for display of said data regarding said operation steps produced by said electrically-powered device (13).

3. The medical apparatus as defined in claim 2, wherein said data monitoring means (14) has at least one key input means (23) for manual operation and control of said display screen and said electrically-powered means (13) and said at least one portable and removable memory card (20) has memory locations associated with said at least one key input means (23).

4. The medical apparatus as defined in claim 3, wherein said electrically-powered device (13) generates perfusion data and said at least one portable and removable memory card (20) has other memory locations for said fixed data and for said perfusion data.

5. The medical device as defined in claim 4, wherein said data monitoring means (14) includes clock circuit means comprising means for changing said data stored on said at least one memory card (20).

6. The medical device as defined in claim 1, wherein said electrically-powered device (13) is a heart-lung machine.

7. The medical device as defined in claim 1, wherein said at least one portable and removable memory card (20) is divided into a plurality of memory blocks of memory locations for perfusion data and fixed data.

* * * * *